(12) United States Patent
McGrath et al.

(10) Patent No.: US 6,844,322 B2
(45) Date of Patent: Jan. 18, 2005

(54) METHOD FOR INDUCED LACTATION

(75) Inventors: Michael F. McGrath, Wildwood, MO (US); Tim H. Klusmeyer, O'Fallin, MO (US); John L. Vicini, Chesterfield, MO (US); Robert H. Schenkel, St. Louis, MO (US); Edward Alan Reed, St. Peters, MO (US); Kanaiyalal R. Patel, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 87 days.

(21) Appl. No.: 09/910,473

(22) Filed: Jul. 20, 2001

(65) Prior Publication Data

US 2002/0058621 A1 May 16, 2002

Related U.S. Application Data

(60) Provisional application No. 60/220,012, filed on Jul. 21, 2000.

(51) Int. Cl.$^7$ ...................... A61K 38/27; A61K 31/566; A61K 31/573
(52) U.S. Cl. .......................................... 514/12; 514/26
(58) Field of Search ..................................... 514/12, 26

(56) References Cited

U.S. PATENT DOCUMENTS

| | | | |
|---|---|---|---|
| 4,060,620 A | 11/1977 | Bauman et al. | 514/171 |
| 4,349,544 A | 9/1982 | Cort et al. | 514/11 |
| 5,182,302 A | 1/1993 | Collier et al. | 514/573 |
| 5,582,592 A | 12/1996 | Kendrick | 604/515 |
| 5,767,080 A | 6/1998 | Beck et al. | 514/12 |
| 6,221,381 B1 | 4/2001 | Shelford et al. | 424/442 |
| 6,224,895 B1 | 5/2001 | Cross | 424/442 |

FOREIGN PATENT DOCUMENTS

WO    WO 94/10200    5/1994

OTHER PUBLICATIONS

Miller et al. J. Dairy Sci., 81 (Suppl. 1): p235 (1998).*
Byatt, J.C., et al. "The Effect of Recombinant Bovine Placental Lactogen on Induced Lactation in Dairy Heifers" *J. Dairy Science* 80: 496–503 (1997).
Cassey, S.M., et al. "Increase in Prolactin Receptor (PRL–R) mRNA Level in the Mammary Gland after Hormonal Induction of Lactation in Virgin Ewes" *Domestic Anim. Endocrin.* 18: 41–55 (2000).
Chakriyarat, S., et al. "Induction of Lactation: Lactational, Physiological, and Hormonal Response in the Bovine" *J. Dairy Science* 61: 1715–1724 (1978).
Collier, R.J., et al. "Effect of Reserpine on Milk Production and Serum Prolactin of Cows Hormonally Induced into Lactation" *J. Dairy Science* 60:896–901 (1977).
Collier, R.J., et al. "Milk Production and Reproductive Performance of Cows Hormonally Induced into Lactation" *J. Dairy Science* 58: 1524–1527 (1975).

Davis, S.R., et al. "Induction of Lactation in Nonpregnant Cows by Estradiol–17β and Progesterone from an Intravaginal Sponge" *J. Dairy Science* 66: 450–457 (1983).
Erb, R.E., et al. "Hormonal Control of Mammogenesis and Onset of Lactation in Cows—A Review" *J. Dairy Science* 60: 155–169 (1976).
Fairclough, R.J., et al. "Dexamethasone Concentrations in Plasma and Milk of Cows Following the Injection of Long- and Short–Acting Dexamethasone Esters" *Aust. J. Biol. Sci.* 34: 313–319 (1981).
Fulkerson, W.J., et al. "Artificial Induction of Lactation in Cattle by Use of Dexamethasone Trimethylacetate" *Aust. J. Biol. Sci.* 28: 183–187 (1975).
Head, H.H. "Artificial Induction of Lactation", in *Biology of Lactation*; Martinet, J.; Houdebine, L.M.; Head, H.H., Eds. INRA: Paris, France: 1999, pp. 227–260.
Kann, G. "Evidence for a mammogenic Role of Growth Hormone in Ewes: Effects of Growth Hormone–Releasing Factor During Artificial Induction of Lactation" *J. Animal Science* 75: 2541–2549 (1977).
Kensinger, R.S. "Induced Lactation: Physiology, Perception, Profitability and Propriety" *J. Dairy Science* 83 (Suppl. 1): 23–24 (2000).
Kensinger, R.S. et al. "Somatotropin Augments Milk Yields of Cows Induced into Lactation" *J. Dairy Science* 81 (Suppl.): 210 (1998).
Kensinger, R.S., et al. "Season and Treatment Effects on Serum Prolactin and Milk Yield During Induced Lactation" *J. Dairy Science* 62: 1880–1888 (1979).
Magliaro, A.L., et al. "Induced Lactation of Nonpregnant Cows or Use of Replacement Heifers: A Profitability Comparison" *J. Dairy Science* 82 (Suppl. 1): 82 (1999).
McFadden, T.B., et al. "Effects of Season on Udder Development and Milk Production of Cows Hormonally–Induced into Lactation" *J. Dairy Science* 78 (Suppl. 1): 203 (1995).

(List continued on next page.)

Primary Examiner—Robert A. Wax
(74) Attorney, Agent, or Firm—Grace L. Bonner; Howrey Simon Arnold & White, LLP (57) ABSTRACT

Methods for effecting mammary secretion of milk from an animal, without the benefit of an immediately preceding pregnancy are provided. An exemplary embodiment the method comprises elevating an animal's estradiol and progesterone blood level sufficient to maintain a milk-secretion stimulating amount for approximately 5 to 12 consecutive days, wherein the day of the first elevation is defined to be day 0; and elevating an animal's somatotropin blood level sufficient to maintain a milk-secretion stimulating amount for at least 20 days from day 0. In any embodiment the method also optionally includes administering to the animal a milk-secretion stimulating amount of dexamethasone on approximately day 13 of the treatment. Furthermore, any embodiment the method may also optionally include adjusting the photo-period to which the animal is exposed in order to stimulate milk secretion. Any embodiment the method may also include physical stimulation of the animal's mammary gland.

16 Claims, 4 Drawing Sheets

OTHER PUBLICATIONS

McFadden, T.B., et al. "Effect of BST on Udder Development and Milk Production of Cows Hormonally–Induced into Lactation" *J. Dairy Science* 78 (Suppl. 1): 203 (1995).

Meites, J. "Farm Animals: Hormonal Induction of Lactation and Galactopoiesis", in *Milk: The Mammary Gland its Secretion. vol. II.;* Kon, S.; Cowie, A.T., Eds. Academic Press, Inc.: New York: 1961, pp 321–367.

Peel, C.J., et al. "The Importance of Prolactin and the Milking Stimulus in the Artificial Induction of Lactation in Cows" *Aust. J. Biol. Sci.*, 31: 187–195 (1978).

Petitclerc, D., et al. "Mammary Growth Response to Holstein Heifers to Photoperiod" *J. Dairy Science* 68: 86–90 (1985).

Smith, K.L.; Schanbacher, F.L. "Hormone Induced Lactation in the Bovine. I. Lactational Performance Following Injections of 17β–Estradiol and Progesterone" *J. Dairy Science* 56: 738–743 (1973).

Smith, R.L., et al. "Efficacy of 17β–Estradiol and Progesterone Treatment to Initiate Lactation in Infertile Cows" *J. Dairy Science* 56:657 [Abstract] (1973).

Smith, K.L.; Schanbacher, F.L. "Hormone Induced Lactation in the Bovine. II. Response of Nulligravida Heifers to Modified Estrogen–Progesterone Treatment" *J. Dairy Science* 57:296–303 (1974).

Stevenson, J. "Are Induced Lactations Worth a Look?" *Hoard's Dairyman*, Nov.: 788 (1998).

Kumar, S. and Ludri, R.S., "Udder development and induction of lactation in repeat breeding multiparous buffaloes treated with estrogen–progesterone and bovine somatotropin," *Indian Journal of Dairy Science* 49:664–672 (1996).

Ferreri, L.F. and Griffith, D.R. "Effect of hypophysectomy and hormone replacement on the DNA and RNA content of experimentally developed rat mammary glands," *J. Endocr.* 74:511–512, (1977).

Harness, J.R. and Anderson, R.R., "Effect of relaxin and somatotropin in combination with ovarian steroids on mammary glands in rats," *Biology of Reproduction* 17:599–603 (1977).

Bellman, O. "Die hormelle Regulation der Laktation," *Klinische Pädiatrie* 188:385–395 (1976). Abstract in English.

Head, H.H. et al. "Effects of various hormone treatments on induction of lactation in the ewe," *Journal of Animal Science* 50:706–712 (1980).

\* cited by examiner

METHOD FOR INDUCED LACTATION

This application claims priority to Provisional Application Ser. No. 60/220,012 filed Jul. 21, 2000.

BACKGROUND OF THE INVENTION

1. Field of the Invention

The present invention relates to the field of enhancing milk production in mammals. More particularly, it concerns pharmaceutical compositions and methods of using said compositions in a manner effective to induce milk production in previously non-lactating animals.

2. Technical Problem Addressed by the Invention

Commercial raising of cattle for dairy production requires proper management. In addition to the various husbandry concerns such as herd health and nutrition, a critical management area for economic survival of any cattle operation, is the breeding management of the cows. In the case of dairy cows, the cows will not produce milk unless they have a calf, which is again dependent upon successful breeding management.

The timing of breeding and breeding intervals generally have great economic significance in dairy operations. Dairy cows are managed intensively and there are costs associated with breeding the cow, how long it takes each cow to become pregnant, as well as associated labor costs; economics of a dairy make it important to both minimize the amount of time a dairy cow is not pregnant and yet still have a high probability of the cow becoming pregnant.

If a cow is successfully bred, she will become pregnant for approximately 280 days. Dairy cows are managed such that they are ideally bred and become pregnant again 45 to 60 days after calving.

It is estimated that for every day past a set goal date that a cow remains non-pregnant or open, there is an economic loss of between $1.00–$3.00 per day. For an average sized dairy herd that is between 200 to 1,000 cows, if the 24 hours during which the cow should be bred is missed for each cow, this represents an economic loss of $4,200.00 to $21,000.00 annually. Often cows are not successfully bred for as many as 3 estrous cycles, due to infertility, infections and semen-related problems. If one half of the cows in a herd of 200 to 1,000 is not impregnated for 3 cycles, the estimated economic loss increases to $6,300.00 to $31,500.00 annually. These projections of economic loss to the producer demonstrate the critical importance of the cow spending the majority of each year producing milk.

Annually 1 million dairy cows are culled for reproductive failure. It is estimated that dairies would retain approximately half of these cows if they were lactating.

To improve the management of dairy cows and decrease the economic losses associated with the non-pregnant interval it is desirable to have additional options and management tools other than culling animals. There is an estimated cost of approximately $900.00 per animal culled for a dairy in addition to the costs incurred for days the animal is at the dairy prior to the decision to replace the animal. The option to be able to selectively use hormonally-induced lactation as a management tool, is desirable. One example of where induced lactation might be an appropriate option is with problem breeder animals of excellent genetic background.

Scientists have been attempting to induce lactation artificially in dairy cows for over 30 years. In general, the studies have involved long hormone administration with low rates of success.

The instant invention provides a method for inducing lactation in a high proportion of mammals; wherein neither the ability to induce lactation, nor the milk yield is affected by the season.

DESCRIPTION OF RELATED ART

It is known that mammary cell proliferation and lactation are both stimulated by ovarian and pituitary hormones (for review see Erb, 1976). Since 1939, attempts have been made to induce lactation (Meites, 1961) using ovarian hormones (or their analogs), but with limited success (milk yields averaging 60% of normal). Substantial progress was made in the 70's when reserpine (Collier et al, 1977) or dexamethasone (Fulkerson et al., 1975) were added to the regimen. Photoperiod (season) also impacts mammary development (Petitclerc, et al., 1985) and this may restrict the ability to artificially induce lactation in countries which utilize seasonal calving. Thus, variability among cows, possible limitations due to day length, and management difficulties surrounding daily injections have resulted in there being only a limited interest in the area of induced lactation.

Davis et al., (1983) described an intra-vaginal sponge for the continuous delivery of ovarian steroids eliminating the need for daily injection. Using this device, the group reported an 89% success rate when an adjunct injection of dexamethasone was given with their regimen. More recently, Kensinger et al., (1998) included POSILAC® somatotropin in the induction protocol and obtained a 17% increase in milk yield compared to cows treated with steroids alone.

Nevertheless, while the induction of lactation has the potential to increase farm profitability by allowing retention of reproductive culls, prior to the present invention, known methods have characteristically produced highly variable results, with respect to both the number of cows that produced milk and the amount of milk they produced (see Head, 1999). While numerous factors, including day length, season of induction, length of dry period, and stage of estrous cycle, have been cited as potentially contributing to this variation (Kensinger, et al., 1979; Peel, et al., 1979; and Smith, et al., 1973), no means for limiting or eliminating the variation had been found prior to the development of the present invention. Therefore, there remains a significant need, in the art, for methods of reproducibly inducing lactation in a high percentage of an animals, regardless of the season.

SUMMARY

The present invention provides methods for effecting mammary secretion of milk in a mammal. The disclosed methods are particularly useful for inducing lactation without the benefit of a immediately preceding pregnancy. The mammal is preferably a bovine. Even more preferably, the mammal is a dairy heifer or a dairy reproductive cull.

In one embodiment, the method comprises administering to an animal an estrogen-like agent (ELA) (e.g. estradiol) and a progestational agent (PGA) (e.g. progesterone) sufficient to maintain a milk-secretion stimulating amount of each agent for approximately 7 consecutive days, wherein the day of the first administration is defined to be day 0; and administering a somatotropin, which is biologically active in the animal, in an amount sufficient to maintain a milk-secretion stimulating amount for 20 or more days from day 0.

In another embodiment the method comprises inducing lactation in a non-pregnant animal by administering to the animal a milk-secretion stimulating amount of an ELA and a PGA for approximately 7 consecutive days, wherein the day of the first administration is defined to be day 0; also administering a milk-secretion stimulating amount of somatotropin for the animal to have bioavailability to the somatotropin for 20 or more days from day 0.

In any embodiment the method may optionally further comprise administering a milk-secretion enhancing amount of a glucocorticoid (e.g. dexamethasone) approximately 6 days after the last ELA administration.

In any embodiment the method may optionally further comprise controlling the photoperiod length the animal is exposed to, either by the use of artificial lighting or selection of time of year when the method is employed, changing the melatonin levels in the animal, or any other effective means.

In any embodiment the method may optionally further comprise physical stimulation of the mammal's mammary gland region for a selected time interval, preferably starting on the day following the last estradiol injection for 7 consecutive days.

In any embodiment somatotropin can be further administered throughout the lactation of the animal.

The instant invention is also directed to a method of using a combination of an ELA, a PGA, natural or synthetic somatotropin, and a glucocorticoid to induce lactation in a non-lactating mammal.

The inventors, surprisingly, discovered that, using the methods described herein, dairy cattle can be induced to lactate and that the effectiveness of that induction is not dependent on the season. Furthermore, lactation can be induced without the benefit of an immediately preceding pregnancy. Consequently, the method is especially useful for inducing lactation in animals which have never been pregnant (such as dairy heifers) and animals which are no longer capable of pregnancy (such as dairy reproductive culls).

DESCRIPTION OF PREFERRED EMBODIMENTS

The present invention is a method for effecting mammary secretion of milk from an animal. As used herein "animal" is defined to include all mammals, including humans. The present invention is particularly useful for inducing lactation in an animal without the benefit of an immediately preceding pregnancy. Thus the present invention is useful for inducing lactation in animals, such as dairy heifers, which have never been pregnant or in animals which are no longer capable of becoming pregnant (e.g. dairy reproductive culls).

As used herein the terms "administer", "administered", and "administration" of the various substances (e.g., progesterone, 17β-estradiol, and etc.), denote providing an additional amount of the substance into the animal's bloodstream on the indicated days, whether via daily or other injections on those days or by release on those days from a parenterally administered prolonged release delivery system (e.g., pellet, liquid depot, vaginal suppository or the like), or by continuous dosing (e.g., by an infusion pump) of the substance, delivered parenterally at the beginning of the time period, or, in the case of the continuous dose, throughout the time period. Alternatively it may refer to the delivery of the dosage by periodic (e.g. daily) parenteral injection or implantation or the like.

As used herein, the terms "milk-secretion stimulating," "milk-secretion enhancing," "milk-secretion maintaining," and "milk-secretion sustaining" amounts of the various treatments to be administered to the animal (i.e. ELA, PGA, somatotropin, dexamethasone, and/or photo-period adjustment), are to be understood as being the amounts of each individual substance or treatment which is required to cause and/or enhance milk-secretion in the presence of the other substances being co-administered. These terms are not meant to indicate the amounts of the individual substance or treatment that would be required to induce milk-secretion by themselves (e.g., treatment with dexamethasone alone).

In each embodiment of the instant invention, the somatotropin administered to the animal is one which is biologically active in said animal. It is proposed that the somatotropin may act, at least partially, by stimulating mammary cell growth and differentiation. This action may be direct, indirect (e.g. through intermediate factors such insulin-like growth factor-1, IGF-1), or both direct and indirect. The Inventor's disclose this possible mode of action for somatotropin, without limiting the invention thereto.

One of ordinary skill in the art will appreciate that the somatotropin may be administered in any manner consistent with the instant invention. The somatotropin is typically given in an amount of approximately 250 mg to 750 mg, with about 500 mg being preferable. The skilled artisan will appreciate that this amount of somatotropin can be delivered in a variety of ways and at a number of different dose levels (depending on the frequency of administration). In a preferred embodiment the somatotropin is administered in a sustained-release formulation. More preferably the somatotropin is administered to the animal until at least day 20 of the treatment, even more preferably until at least day 30 (e.g. on days 0, 10, 20 and 30). Most preferably somatotropin is administered as a sustained release dose throughout lactation.

Those skilled in the art will also recognize that any natural or synthetic analog of the somatotropin having approximately the equivalent bioactivity of the somatotropin native to the animal (e.g. bovine somatotropin used in cattle) may also be used. Approximately equivalent bioactivity as used herein would be at least 50% of the bioactivity of the somatotropin. Preferably such analog would have at least 75% of the equivalent bioactivity, more preferably 90% of the equivalent bioactivity and most preferably 100% or greater than 100% of the bioactivity equivalent to the somatotropin.

Although 17β-estradiol is used as the ELA in the exemplary embodiments herein, those skilled in the art will recognize that the ELA may be any natural or synthetic analog of 17β-estradiol or any other substance having, when administered to the animal, a bioactivity approximately equivalent to the bioactivity of 17β-estradiol. As used herein the term "bioactivity" refers to the ability to produce a physiological response in the animal. An "approximately equivalent bioactivity" as used herein would be at least 50% of the equivalent bioactivity of 17β-estradiol. Preferably such analog would have at least 75% of the equivalent bioactivity, more preferably 90% of the equivalent bioactivity and most preferably 100% or greater than 100% of the bioactivity equivalent to 17β-estradiol. The ELA may be given in any dose that is consistent with the present invention. Preferably, the ELA is provided in a dose of approximately 0.007 to 0.7 mg/kg body weight, more preferably about 0.07 to 0.7 mg/kg body weight, most preferably about 0.7 mg/kg body weight.

Similarly, although progesterone is used as the PGA in the exemplary embodiments herein, those skilled in the art will recognize that PGA may be any natural or synthetic analog of a progesterone or any other substance having, when administered to the animal, a bioactivity approximately equivalent to the bioactivity of the progesterone. An "approximately equivalent bioactivity" as used herein would be at least 50% of the equivalent bioactivity of progesterone. Preferably such analog would have at least 75% of the equivalent bioactivity, more preferably 90% of the equivalent bioactivity and most preferably 100% or greater than 100% of the bioactivity equivalent to progesterone. The PGA may be given in any dose that is consistent with the present invention. Preferably, the ELA is provided in a dose of approximately 0.0175 to 1.75 mg/kg body weight, more preferably about 0.175 to 1.75 mg/kg body weight, most preferably about 1.75 mg/kg body weight.

The ELA and PGA may be delivered by any means consistent with the instant invention. In one embodiment of the invention the ELA and PGA are administered parenterally as a pellet at the beginning of the treatment. In a preferred embodiment of this aspect of the invention the ELA are subcutaneously implanted as a slow release pellet. Even more preferably the ELA and PGA are respectively 17β-estradiol and progesterone and are administered subcutaneously as slow-release pellets, wherein the 17β-estradiol pellet comprises approximately 0.7 mg/kg body weight 17β-estradiol, and wherein the progesterone pellet comprises approximately 1.75 mg/kg of body weight progesterone In an alternative embodiment of the invention the ELA and PGA are injected subcutaneously twice daily (approximately every 12 hours) for 5–12 consecutive days, preferably 7 consecutive days. In a preferred aspect of this embodiment of the invention the ELA and PGA are respectively 17β-estradiol and progesterone delivered at a dose of approximately 0.001 to 0.1 mg/kg body weight, preferably 0.01 to 0.1 mg/kg body weight 17β-estradiol and 0.0025 to 0.25 mg/kg body weight 0.025 to 0.25 mg/kg body weight progesterone.

ELA and PGA administration should be sufficient to produce and maintain blood ELA and PGA levels, at concentrations sufficient to stimulate milk-secretion. Preferably, the ELA and PGA levels are maintained over a period of approximately 5 to 12 days, with 7 days being most preferable in cows.

Any embodiment may optionally further comprise the use of a single administration of a milk-secretion enhancing amount of a glucocorticoid. Preferably, the glucocorticoid is dexamethasone, nevertheless, the ordinarily skilled artisan will appreciate that other glucocorticoids may function in a similar fashion. Typically, dexamethasone is administered, to the animal, on about day 10 to about day 17 of the treatment, preferably approximately 7 days after the discontinuation of the ELA and PGA. More preferably, the dexamethasone is administered on approximately day 13 of the treatment. It is believed that, when used, dexamethasone It is believed that the glucocorticoid treatment acts, at least partially by ensuring that the mammary gland cells differentiate fully from the "growing state" to the "milk-secreting" state. During normal gestation, this differentiation takes place near parturition as the glucocorticoid levels rise and the glands begin to secrete milk. Thus, it is proposed that when the glucocorticoid (e.g. dexamethasone) is administered to the animal, in accordance with the methods of the instant invention, the increased glucocorticoid level in the animal enhances the function of one or more of the cellular signaling cascades involved in orchestrating the physiological changes which must occur before milk production can begin. The Inventor's disclose this possible mode of action for the glucocorticoid, without limiting the invention thereto. The glucocorticoid is typically given at a dose of approximately 0.005 to 0.5 mg/kg body weight, preferably, approximately 0.05 to 0.5 mg/kg, and most preferably approximately 0.05 mg/kg.

Those skilled in the art will also recognize that any natural or synthetic glucocorticoid having approximately the equivalent bioactivity of dexamethasone may also be used. Approximately equivalent bioactivity as used herein would be at least 50% of the bioactivity of dexamethasone. Preferably such analog would have at least 75% of the equivalent bioactivity, more preferably 90% of the equivalent bioactivity and most preferably 100% or greater than 100% of the bioactivity equivalent to dexamethasone.

Any embodiment may optionally further comprise controlling the amount of photoperiod to which the animal is exposed. Those skilled in the art will recognize that some species of animal have seasonal fertility (e.g., animals such as sheep are only fertile during specific times of the year) which is influenced by length of photoperiod. Some animals are more fertile during decreasing photoperiods and some animals have increasing fertility in response to increasing photoperiod. The amount of photoperiod can be influenced by the use of housing with artificial lights, for example. A fixed photoperiod may be used in the embodiments or a schedule of changing photoperiod, i.e., increasing or decreasing photoperiod may be employed, depending on the animal and the desired level of response.

Any embodiment may optionally include starting the treatment method at a specific time in a female animal's reproductive cycle. Those skilled in the art will know that reproductive status and cycle can be easily determined, and if desired, synchronized by the use of an appropriate regimen of reproductive hormone administration. Such schedules and management are well know in the art.

Any embodiment may optionally include physical stimulation of the mammary gland. The mammary gland stimulation is preferably administered at least once daily starting on about day 6 of the treatment (as counted from a treatment beginning on day 0) and continuing for at least 7 consecutive days. More preferably the physical stimulation is administered twice daily at approximately evenly spaced intervals and most preferably the mammary gland is stimulated three times a day at approximately evenly spaced intervals. The physical stimulation may be administered or applied in the form of manually massaging of the mammary gland (the udder, in the case of cows) or by application of a mild, intermittent vacuum, such as the attachment of the milking cups of an automatic milking machine.

It is also to be recognized that alternate modes of administration of the ELA, PGA, somatotropin, and, when optionally included, the dexamethasone may be employed. Such modes of administration include for example, but are not limited to osmotic pump, injection, pellet, pessary, oral, implant, suppository, aerosol, transdermal administration and the use of other delivery devices, which can either be removed at a desired time or used until exhausted of content.

In one preferred embodiment the animal of the method is a dairy heifer that has never been pregnant. In some embodiments it is desirable to use animals that appear to be temporarily or permanently infertile. Those skilled in the art will recognize that the invention may also be employed on animals that are non-pregnant but in declining lactation at the onset of use of the method.

EXAMPLE 1

Effect of season on induction of lactation was assessed with multiparous cows induced in February (FEB, n=15) or June (JUN, n=18). All cows were reproductive culls which had completed at least one lactation and had obtained an "adjusted milk yield" (305ME) of at least 8,182 kg in their previous lactation. Treatments started on day 0 and consisted of twice daily injections of 17β-estradiol (0.1 mg/kg BW/d) (i.e. 0.1 mg estradiol/kg of body weight/day) and progesterone (0.25 mg/kg BW/d) for 7 d, twice daily mammary massage (2–3 min/gland) for the next 6 days, and an injection of dexamethasone (0.05 mg/kg BW/d) on day 13 of study. Cows also received somatotropin (POSILAC 1 STEP®, 500 mg bST) on days 0, 10, 20, and 30 of study and at 14 d intervals thereafter (see Table 1).

TABLE 1

Treatment Schedule for Induction of lactation

| Treatment | Dose | Day of Study | Delivery Route |
|---|---|---|---|
| 17β-estradiol[a] | 0.1 mg/kg body weight | 0–6 | subcutaneous |
| Progesterone[a] | 0.25 mg/kg body weight/day | 0–6 | subcutaneous |
| bovine somatotropin (POSILAC ®)[b] | 500 mg | 0, 10, 20, 30, and about every 14 days thereafter | subcutaneous |
| Dexamethasone[c] | 0.05 mg/kg body weight | 13, administered ~24 hours prior to first milking | intramuscular |

[a]Sigma, St. Louis Missouri, administered at ~12 hour intervals
[b]Monsanto, St. Louis Missouri
[c]Schering-Plough Kenilworth, New Jersey.

Milking (3 times/day) commenced on day 14 of study and continued for 122 days. Samples from each milking on a single day in weeks 1, 2, 3, 4, 8, 12 and 16 of lactation were collected for analyses. Cows were considered non-responsive and removed if they failed to produce ≧9.1 kg of milk on a single day by the 24$^{th}$ day of lactation. Induction was successful if at least one daily total milk yield was ≧13.6 kg by the 50$^{th}$ day of lactation. Two cows failed to respond in each season and one JUN cow responded but was removed for health reasons on day 12 of lactation. Thus, induction was successful in 13 of 15 (86.7%) FEB cows and 15 of 18 (83.3%) JUN cows. Of these cows, one FEB and two JUN cows were removed prior to day 70 of lactation for health reasons. Single milk samples (first milking of the day) were collected from day 1–8 of lactation and analyzed for progesterone and estrogen content (respectively FIG. 6 and FIG. 7). Additionally, tail vein blood samples were collected from JUN cows on day −6, −3, 0, 1, 4, 4, 14, 21, 29, 42, 56, 70, 84, and 112 of lactation. Blood samples were also collected from a group of non-induced, multiparous cows that calved during the two week period when the induced cows received treatments to initiate lactation. All blood samples were analyzed for non-esterified fatty acid (NEFA) content using the NEFA-C® kit (Wako Chemicals, Neuss, Germany). The JUN induced cows tended (P<0.1) to have greater NEFA concentrations than cows that calved and lactated during the same season.

Figure 1:
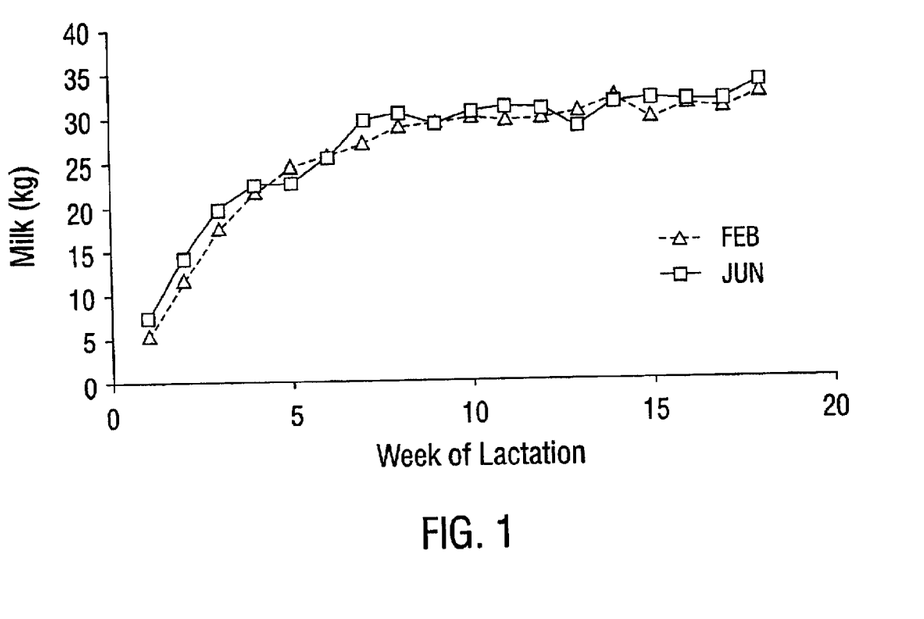
FIG. 1 is a graph comparing the weekly average milk production for cows induced into winter-phase (FEB) and summer-phase (JUN) lactation as described in Example 1.

The shape of the lactation curve was similar for both seasons (see FIG. 1). Total 122 day yields of actual milk (2966, 2729 kg), 3.5% Fat-corrected milk (FCM) (3077, 2964 kg), and 4.0% solids-corrected milk (SCM) (2875, 2722 kg) did not differ between seasons. Daily yield per cow averaged 25.0 kg milk, 27.6 kg FCM, and 25.5 kg SCM. Milk composition did not differ between FEB and JUN cows. Milk was discarded from day 0 to day 28 of the study (day 1–14 of lactation). Milk samples were collected from all three milkings on day 7, 14, 21, 28, 56, 84, and 112 of lactation, preserved with 2-bromo-2-nitropropane-1,3diol, and analyzed within two days for fat, total protein, lactose, and somatic cells (see Table 2).

TABLE 2

Yield and composition of milk from Holstein reproductive culls induced to lactate in late winter (FEB) and early summer (JUN)

| Item | FEB | JUN | P-value |
|---|---|---|---|
| Milk Yield-total (kg) | | | |
| Actual Milk | 2,966 | 2,729 | 0.8 |
| 3.5% FCM | 3,077 | 2,964 | 0.9 |
| 4.0% SCM | 2,875 | 2,722 | 0.9 |
| Milk yield-daily (kg/d) | | | |
| Actual Milk | 25.3 | 24.7 | 0.8 |
| 3.5% FCM | 27.4 | 27.7 | 0.9 |
| 4.0% SCM | 25.6 | 25.4 | 0.9 |
| Milk composition | | | |
| Fat (%) | 4.0 | 4.5 | 0.3 |
| Protein[a] (%) | 3.5 | 3.4 | 0.2 |
| Lactose (%) | 4.9 | 4.9 | 0.4 |
| Somatic Cells (10$^3$/ml) | 159 | 141 | 0.8 |

[a]Measured as total protein

Figure 2:
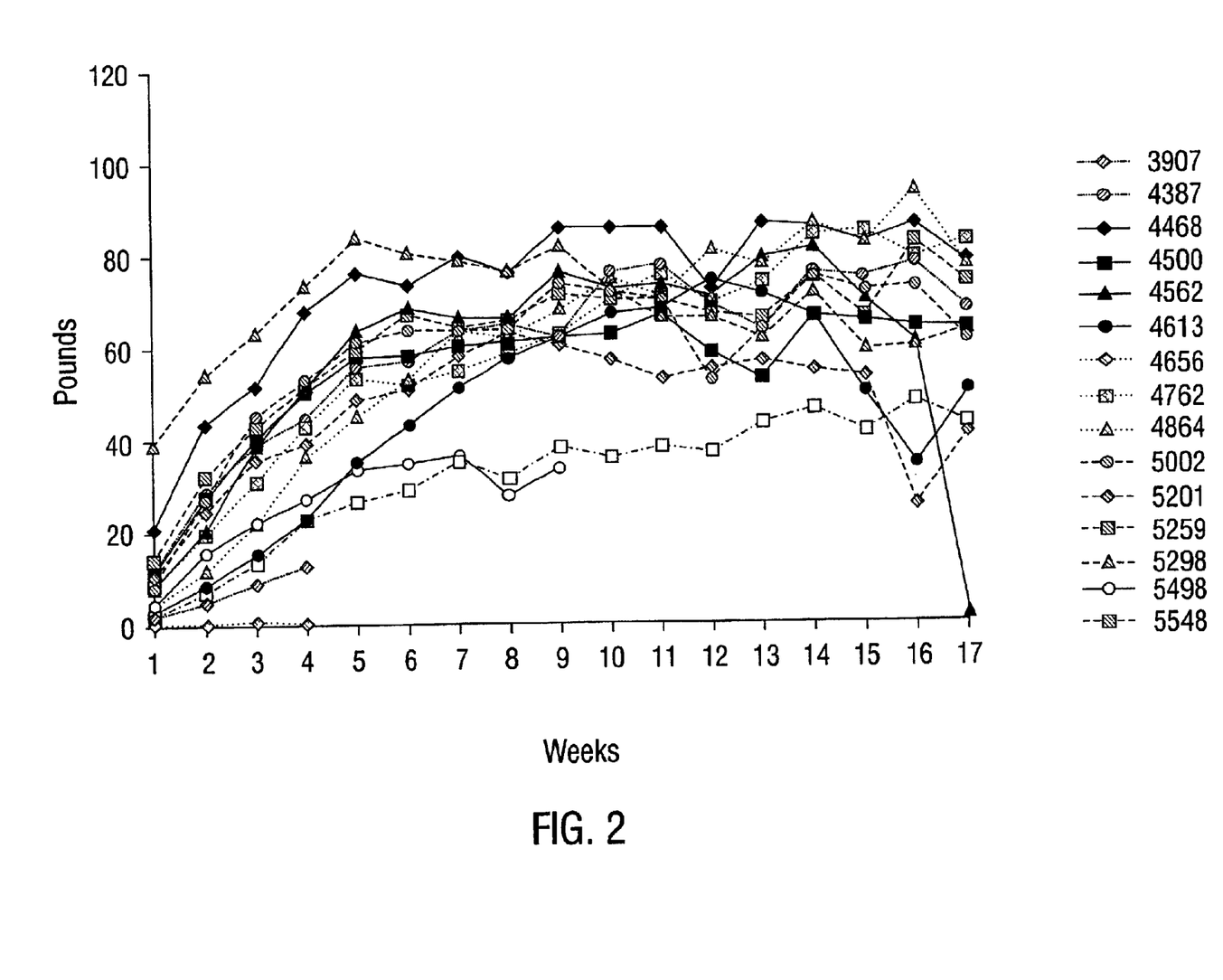
FIG. 2 is a graph showing the weekly average milk production for each individual cow induced into winter-phase lactation in Example 1.
Figure 3:
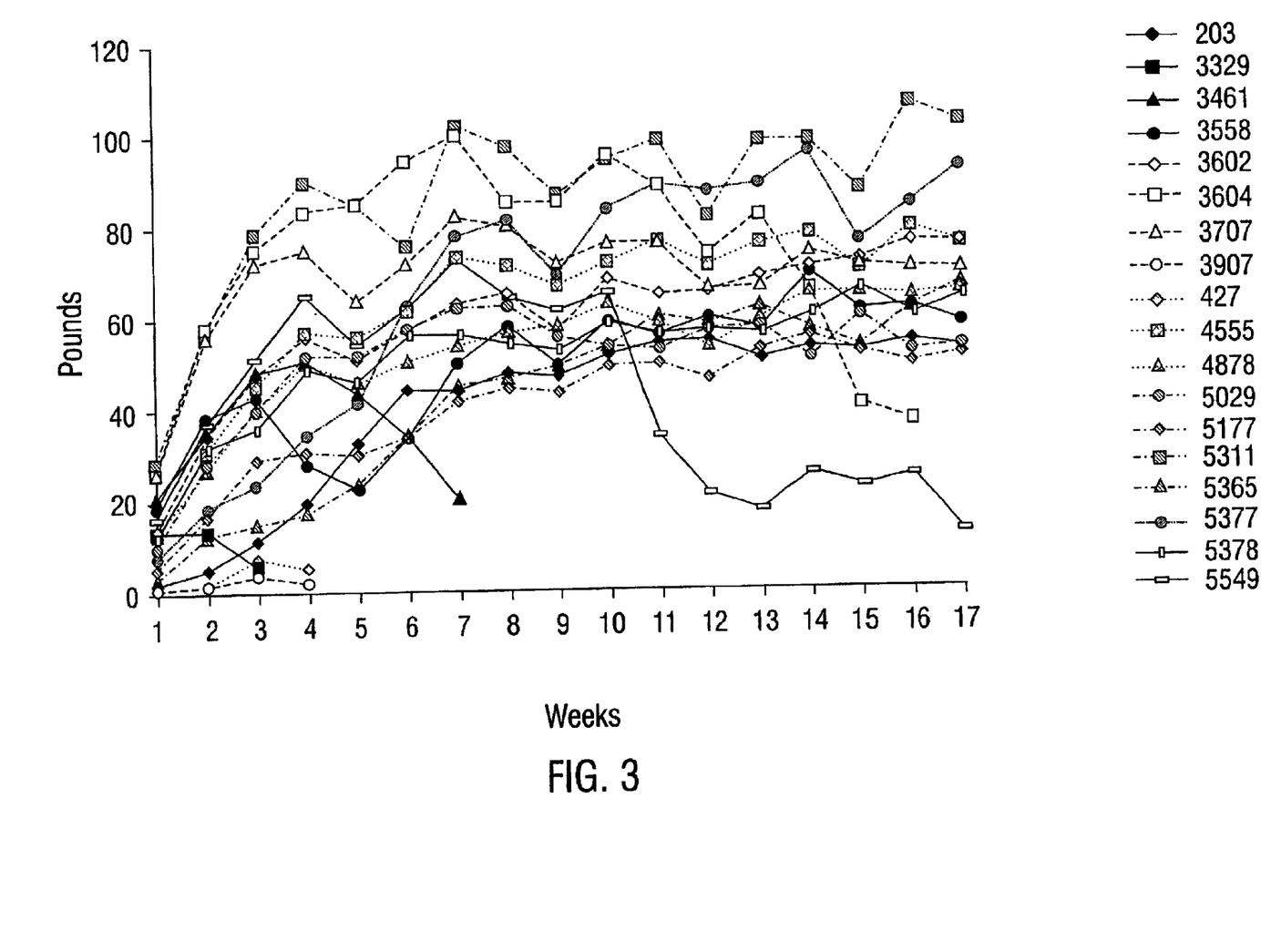
FIG. 3 is a graph showing the weekly average milk production for each individual cow induced into summer-phase lactation in Example 1.
Figure 4:
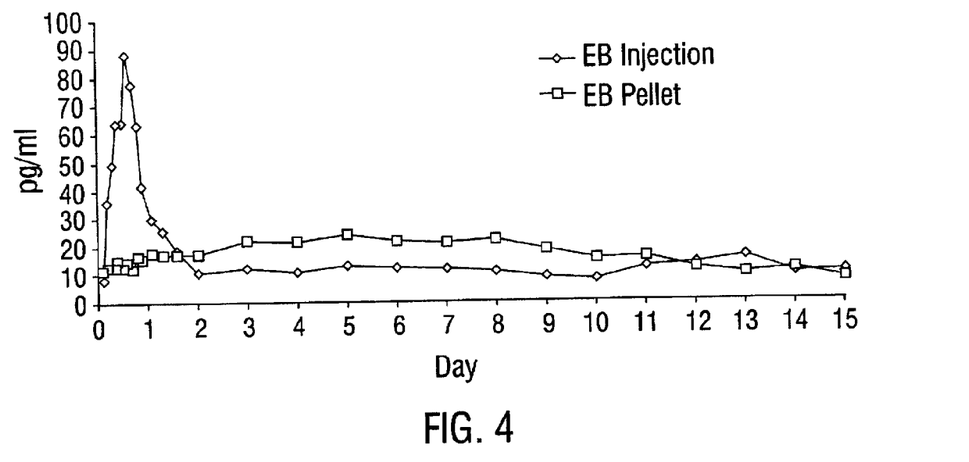
FIG. 4 is a graph showing plasma estradiol in animals implanted with pelleted estradiol benzoate or given an estradiol injection (2 mg on day 0).
Figure 5:
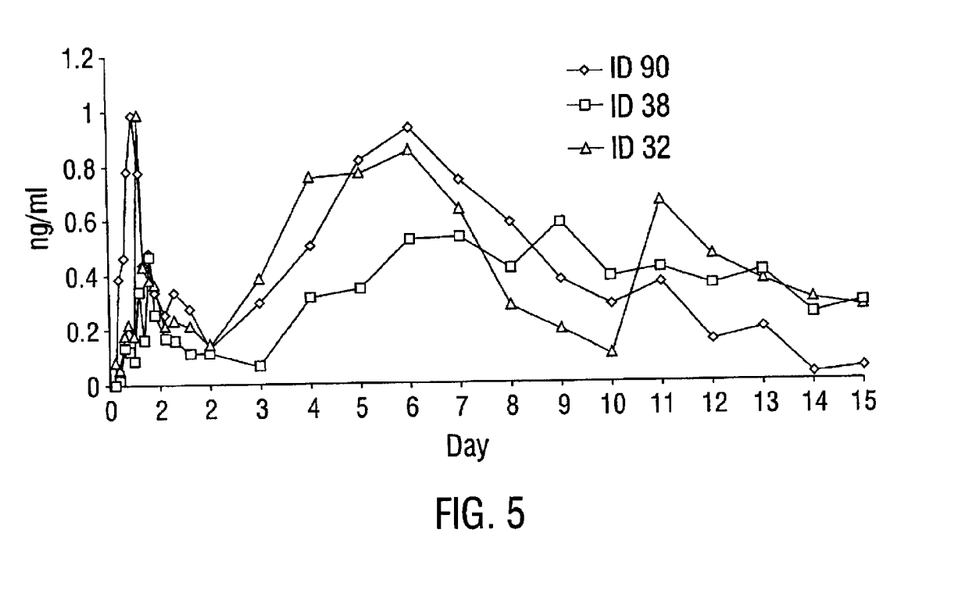
FIG. 5 is a graph showing plasma progesterone in animals implanted with pelleted progesterone (100 mg on day 0).

In this study, induction was successful in 13 of 15 of FEB cows (86.7%) and 15 of 18 JUN cows (83.3%). The shape of the lactation curve was similar for both seasons (FIG. 1) with cows attaining a plateau (about 30 kg of milk/day) by week eight of lactation. Milk yield and composition did not significantly differ between seasons (Table 2). Furthermore, the results also showed that about 70% of the cows treated using this embodiment surprisingly produced more than 60 lbs. of milk/day and at times averaged production of over 70 lbs. of milk/day (see FIGS. 2 and 3). Surprisingly, the cows' milk yield was not affected by season. Regardless of the season of induction, adjusted milk yields (305ME) of the induced cows averaged 65% of their 305ME from the previous lactation (Table 3).

TABLE 3

Adjusted milk yield (305ME) of Holstein reproductive culls during either their induced lactation or after a previous calving

|  | Previous | Induced | |
| --- | --- | --- | --- |
|  | Yield (kg) | Yield (kg) | % of previous yield |
| FEB | 13,257 | 8,329 | 62.8 |
| JUN | 12,065 | 8,004 | 66.3 |

EXAMPLE 2

Example 2 is a prophetic example using a single administration of 17β-estradiol and single administration of progesterone.

Simple pellets of estradiol benzoate containing approximately 525 mg of estradiol per pellet are produced by compression with an appropriate carrier and administered subcutaneously, the day of administration being defined as day 0. Progesterone pellets containing approximately 1312 mg progesterone per pellet are similarly produced and are administered subcutaneously on day 0. Estradiol is substantially elevated for 10 days in animals administered estradiol pellets. Progesterone is substantially elevated for 7 to 8 days in animals administered progesterone pellets.

A single dose of dexamethasone is given as an intramuscular (IM) injection on day 13. Sustained-release somatotropin (POSILAC®) is administered subcutaneously on days 0, 10,20,30 and every 14 days after day 30. From day 7 to day 13 udders were messaged twice daily. Milk production is measured for 119 days.

The animals in this example exhibit a surprising response to the method of the present invention, as measured in pounds of milk produced by each animal.

A significant number of the animals produced 30 lb. of milk per day within their first 50 days in milk. The majority of the animals produce greater than 30 lb. of milk per day. By the end of the trial a substantial majority of the cows are averaging 65 lb. of milk per day and surprisingly a majority of the cows were averaging 70 lb. of milk per day. These results are surprising both because of the number of animals that respond to the method and because of the level of response in each animal, as measured in amount of milk produced per day.

While there is shown and described the a number of exemplary embodiments of the invention, it is to be distinctly understood that this invention is not limited thereto but may be variously embodied to practice the invention.
References:

The following references, to the extent that they provide exemplary procedural or other details supplementary to those set forth herein, are specifically incorporated herein by reference.

Byatt, J. C., R. H. Sorbet, P. J. Eppard, T. L. Curran, D. F. Curran and R. J. Collier. 1997. *The effect of recombinant bovine placental lactogen on induced lactation in dairy heifers.* J. Dairy Sci., 80:496–503.

Cassey, S., M. Charlier, L. Belair, M. Guillomot, K. Laud and J. Djiane. 2000. *Increase in prolactin receptor (PRL-R) mRNA level in the mammary gland after hormonal induction of lactation in virgin ewes.* Domestic Anim. Endocrion. 18:41–55.

Chackriyarat, S., H. H. Head, W. W. Thatcher, F. C. Neal, and C. J. Wilcox. 1978. *Induction of lactation: Lactational, physiological, and hormonal responses in the bovin.* J. Dairy Sci. 61:7115–7124.

Collier, R. J., D. E. Bauman and R. L. Hays. 1977. *Effect of reserpine on milk production and serum prolactin of cows hormonally induced into lactation.* J. Dairy Sci. 60:896–901.

Collier, R. J., D. E. Bauman and R. L. Hays. 1975. *Milk production and reproductive performance in cows hormonally induced into lactation.* J. Dairy Sci. 58:1524–1527.

Davis, S. R., R. A. S. Welch, M. G. Pearce and A. J. Peterson. 1983. *Induction of lactation in nonpregnant cows by estradiol 17-β and progesterone from an intravaginal sponge.* J. Dairy Sci. 66:450–457.

Erb, R. E. 1976. *Hormonal control of mammogenesis and onset of lactation in cows-A review.* J. Dairy Sci., 60:155–169.

Fulkerson, W. J. and G. H. McDowell. 1975. *Artificial induction of lactation in cattle by use of dexamethasone trimethylacetate.* Aus. J. Biol. Sci. 34:1 93–187.

Head, H. H. 1999. *Artificial induction of lactation.* pp. 227–260. in Biology of Lactation, J. Martinet, L. M. Houdebine and H. H. Head, ed. INRA, Paris, France.

Kann, G. 1977. *Evidence for a mammogenic role of growth hormone in ewes: effects of growth hormone-releasing factor during artificial induction of lactation.* J. Anim. Sci. 75:2541–2549.

Kensinger, R. S. 2000. *Induced lactation: physiology, perception, profitability and propriety* J. Dairy Sci. 83 (Suppl. 1):23.

Kensinger, R. S., R. Grabowski and A. L. Magliaro. 1998. *Somatotropin augments milk yields of cows induced into lactation.* J. Dairy Sci. 81(Suppl.): 210.

Kensinger, R. S., D. E. Bauman and R. J. Collier. 1979. *Season and treatment effects on serum prolactin and milk yield during induced lactation.* J. Dairy Sci. 62:1880–1888.

Magliaro, A. L., Ford, S. A., O'Conner, M. L., Muller, L. D., Graboskiand, R., and R. S. Kensinger 1999. *Induced lactation of nonpregnant cows or use of replacement heifers: a profitability comparison.* J. Dairy Sci. 82 (Suppl. 1):82.

McFadden, T. B., B. A. Clark and R. C. Hovey. 1995. *Effects of BST on udder development and milk production of cows hormonally induced into lactation.* J. Dairy Sci. 78 (Suppl. 1):203.

McFadden, T. B., B. A. Clark and R. C. Hovey. 1995. *Effects of season on udder development and milk production of cows hormonally induced into lactation.* J. Dairy Sci. 78 (Suppl. 1):203.

Meites, J. 1961. *Farm animals: hormonal induction of lactation and galactopoesis.* Page 321 in S. Kon and A. T. Cowie, ed Milk: The mammary gland and its secretion. Vol. II. Academic Press Inc., New York and London.

Peel, C. J., J. W. Taylor, I. B. Robinson, A. A. McGowan, R. D. Hooley and J. K. Findlay. 1979. *The use of oestrogen, progesterone and reserpine in the artificial induction of lactation in cattle.* Aust. J. Biol. Sci. 31:187–195.

Petitclerc, D., R. D. Kineman, S. A. Zinn and H. A. Tucker. 1985. *Mammary growth response of Holstein heifers to photoperiod* J. Dairy Sci. 68:86–90.

Smith, K. L., D. R. Redman and F. L. Schanbacher. 1973. *Efficacy of 17β-estradiol and progesterone treatment to initiate lactation in infertile cows.* J. Dairy Sci. 56: 657 (Abstract).

Smith, K. L. and F. L. Schanbacher. 1973. *Hormone induced lactation in the bovine I. Lactational performance follow-* ing injections of 17β-estradiol and progesterone. J. Dairy Sci. 56:738–743.

Smith, K. L. and F. L. Schanbacher. 1974. *Hormone induced lactation in the bovine II. Response of nulligravida heifers to modified estrogen-progesterone treatment.* J. Dairy Sci. 57:296–303.

Stevenson, J. 1998. *Are induced lactations worth a look?* Hoard's Dairyman November:788.

What is claimed is:

1. A method of inducing milk production in a mammal, the method comprising:

administering to the mammal, to induce lactation, a milk-secretion stimulating amount of:

i) an estrogen-like agent (ELA); and a progestational agent (PGA); wherein the first day of administration is defined as day 0; and ii) a biologically active somatotropin (ST); wherein the somatotropin is administered to the manunal to provide bioavailability of a milk-secretion stimulating amount beginning on day 0 and continuing for 20 days or more and continues beyond the induction of lactation;

wherein the mammal is a bovine selected from the group consisting of dairy heifers and dairy reproductive culls.

2. The method of claim 1 wherein the ELA and PGA are administered as either a single sustained-release dose or are administered for approximately 5–12 days, beginning on day 0.

3. The method of claim 2 wherein the ELA is adminstered at a dose of approximately 0.001 to 0.1 mg/kg/day and the PGA is administered at a dose of approximately 0.0025 to 0.25 mg/kg/day and is administered for approximately seven days.

4. The method of claim 2 wherein the somatotropin is administered for at least 30 days from day 0.

5. The method of claim 4 wherein the somatotropin is administered in approximately 4 doses.

6. The method of claim 4 wherein the somatotropin is further administered in a sustained-release dose approximately every 14 days throughout lactation.

7. The method of claim 1, further comprising administering a milk-secretion enhancing amount of a glucocorticoid.

8. The method of claim 7 wherein the glucocorticoid is administered either on approximately day 10 to day 17 of the treatment or approximately 6 days after the final ELA administration.

9. The method of claim 7 wherein the glucocorticoid is dexamethasone administered at a dose of approximately 0.005 to 0.5 mg/kg on approximately day 10 to day 17 of the treatment.

10. The method of claim 1, further comprising subjecting the mammal to milk-stimulating photoperiods starting on, or before, day 0.

11. The method of claim 10 wherein said photoperiods:

a) comprise 12 consecutive hours of light and 12 consecutive hours of dark during each 24 hour period;

b) comprise progressively longer periods of light during each successive 24 hour period; or c) comprise progressively shorter periods of light during each successive 24 hour period.

12. The method of claim 1 further comprising providing physical stimulation of the mammal's mammary gland region at least once daily for at least 7 consecutive days, starting on approximately day 7 of the treatment.

13. The method of claim 12 wherein the mammals mammary gland region is stimulated at least three times daily.

14. A method of inducing milk production in a mammal, the method comprising:

administering to the mammal, to induce lactation:

i) an estrogen-like agent (ELA), subcutaneously, at a dose of approximately 0.007 to 0.7 mg/kg/body weight;

ii) a progestational agent (PGA), subcutaneously, at a dose of approximately 0.0175 to 1.75 mg/kg/body weight/;

iii) a glucocorticoid, intramuscularly, at a dose of approximately 0.005–0.50 mg/kg/body weight; and iv) a biologically active somatotropin, subcutaneously, at a dose of approximately 250–750 mg;

wherein ELA and PGA doses are each administered beginning on day 0; wherein the glucocorticoid dose is administered on approximately day 10 to 17; wherein the first day of treatment is designated day 0 (zero); wherein the somatotropin is administered beginning on day 0 and periodically thereafter as required to maintain the bioavailability of a milk-secretion stimulating amount through at least day 20 of the treatment and continues beyond the induction of lactation; and wherein the mammal is selected from the group consisting of dairy heifers and dairy reproductive culls.

15. The method of claim 1 wherein with the ELA is 17β-estradiol administered on day 0, as a slow-release pellet, at a dose of approximately 0.7 mg/kg body weight, wherein the PGA is natural progesterone administered on day 0, as a slow release pellet, at a dose of approximately 1.75 mg/kg body weight; wherein the somatotropin is administered as a sustained-release pellet approximately every two weeks throughout lactation; wherein the method further comprises administering, intramuscularly, dexamethasone on day 13, at a dose of approximately 0.05 mg/kg body weight; and wherein the treatment further comprises stimulating the mammary gland of the heifer or cull at least 2 times daily for at least seven consecutive days beginning on approximately day 7.

16. The method of claim 14 wherein the glucocorticoid is dexamethasone.

\* \* \* \* \*